United States Patent [19]

Toussaint et al.

[11] Patent Number: 4,699,622
[45] Date of Patent: Oct. 13, 1987

[54] DISPOSABLE DIAPER HAVING AN IMPROVED SIDE CLOSURE

[75] Inventors: John W. Toussant, West Chester; Margaret H. Hasse, Wyoming, both of Ohio

[73] Assignee: The Procter & Gamble Company, Cincinnati, Ohio

[21] Appl. No.: 842,326

[22] Filed: Mar. 21, 1986

[51] Int. Cl.⁴ ............................................ A61F 13/16
[52] U.S. Cl. .................................................... 604/389
[58] Field of Search ................. 604/385.1, 385.2, 389, 604/390, 391

[56] References Cited

U.S. PATENT DOCUMENTS

| | | | |
|---|---|---|---|
| 2,931,747 | 4/1960 | Dexter | 640/389 |
| 3,359,980 | 12/1967 | Rosenblatt . | |
| 3,610,244 | 10/1971 | Jones, Sr. | 604/390 |
| 3,638,651 | 2/1972 | Torr . | |
| 3,776,232 | 12/1973 | Schaar . | |
| 3,848,594 | 11/1974 | Buell . | |
| 4,122,552 | 10/1978 | Tedford . | |
| 4,253,461 | 3/1981 | Strickland . | |
| 4,402,688 | 9/1983 | Julemont | 604/385.2 |
| 4,516,976 | 5/1985 | Bell | 604/389 |

Primary Examiner—John D. Yasko
Attorney, Agent, or Firm—John M. Pollaro; Fredrick H. Braun; Richard C. Witte

[57] ABSTRACT

A disposable diaper having an improved side closure is disclosed. The disposable diaper is provided with an outer fastening means and an inner fastening means. The outer fastening means maintains the waist portions of the diaper in an overlapping configuration while the inner fastening means reduces shifting of the overlapping portions.

9 Claims, 2 Drawing Figures

DISPOSABLE DIAPER HAVING AN IMPROVED SIDE CLOSURE

BACKGROUND OF THE INVENTION

This invention relates to disposable diapers having elasticized leg openings, and more particularly to an improved side closure for such disposable diapers. Still more particularly, this invention relates to an improved side closure for disposable diapers having elasticized leg openings comprising an outer fastening means and an inner fastening means.

Disposable diapers are well known articles of manufacture which are worn by infants and incontinent persons. Disposable diapers are worn about the lower torso and are intended to absorb and contain urine and feces thereby preventing the urine and feces from soiling, wetting, or otherwise contaminating the articles (e.g., clothing, bedding, etc.) which come into contact with the diaper wearer.

In general, disposable diapers all have the same basic structure which comprises an absorbent core encased between a liquid permeable user contacting topsheet and a liquid impermeable backsheet. The prior art, of course, teaches numerous variations of and elements in addition to the basic topsheet, backsheet, and absorbent core arrangement. For example, an improvement in the performance of disposable diapers has been achieved by the addition of an elastic means along that portion of the disposable diaper which contacts the wearer's thigh thereby providing elasticized leg openings when the diaper is worn.

When using a disposable diaper having elasticized leg openings the diaper user fits the diaper on the wearer and fastens it about the wearer's waist thereby effecting a side closure. Fitting the diaper about the wearer usually requires the front and back waist portions of the diaper to overlap each other. As the diaper is worn the movements of the wearer and the forces induced by the elastic means at the leg openings tend to cause the overlapping front and back waist portions to shift position relative to each other. In other words, overlapping front and back waist portions are subjected to forces which tend to cause the front and back waist portions to assume a position relative to each other which is different from the position they assume when the diaper is initially fitted to the wearer. Unless such shifting is limited the fit and containment characteristics of the diaper are degraded as the diaper is worn.

A number of concepts have been proposed for fastening a disposable diaper about the waist of the wearer. For example, U.S. Pat. No. 3,848,594, which issued to K. B. Buell on Nov. 19, 1974, teaches a tape fastening system for effecting a side closure in disposable diapers which has an improved manufacturers joint (i.e., the attachment between the fastener tape and the diaper which is made by the manufacturer). U.S. Pat. Nos. 3,359,980 which issued to C. L. Rosenblatt on Dec. 26, 1967 and 3,638,651 which issued to D. Torr on Feb. 1, 1972 both teach diapers in which a side closure is effected by overlapping portions of the diaper. Additional side closures are described in U.S. Pat. Nos. 3,776,232 which issued to C. H. Schaar on Dec. 4, 1973 and 4,122,552 which issued to F. Tedford on Oct. 31, 1978. Both the Tedford and Schaar patents are directed to improving the side closure by affixing the front and back waist portions together over a relatively large area. The Schaar patent achieves this result by using two fastening mechanisms while the Tedford patent uses a single fastening system which covers a relatively large area.

None of the foregoing patents are specifically directed to disposable diapers having elasticized leg openings and the special problems of maintaining good fit characteristics associated with such diapers. U.S. Pat. No. 4,253,461 which issued to D. L. Strickland et al. on Mar. 3, 1981, is directed to a disposable diaper having elasticized leg openings and achieves an improved side closure by providing separate fastening means at the waist and at the thigh.

The disposable diapers of the prior art lack the aspects of the present invention whereby an improved side closure having an outer fastening means and an inner fastening means is provided which means together prevent relative motion between the front and back waist portions.

It is therefore an object of the present invention to provide an improved side closure for disposable diaper having elasticized leg openings.

A further object of the present invention is to provide an improved side closure which maintains the fit of the diaper at the waist and at the elasticized leg openings during wearing.

An additional object of the invention is to provide a disposable diaper having elasticized leg openings which has improved urine and feces containment characteristics.

These and other objects of the invention will be more readily apparent when considered in reference to the following description and when taken in connection with the accompanying drawings.

SUMMARY OF THE INVENTION

According to the present invention, a disposable diaper having elasticized leg openings is manufactured such that an absorbent means is encased between a liquid permeable topsheet and a liquid impermeable backsheet. A portion of the contractive force generated by the elastic means used at the leg openings of such diapers is directed into the waist portion of the diaper. These forces together with the movements of the diaper wearer tend to cause shifting of the front and back waist portions. Shifting, as used herein, is the movement of the front and back waist portions relative to each other from the position they assume when the diaper is initially applied. When such relative motion occurs the fit about the wearers legs and waist becomes looser and less effective in containing waste products.

The disposable diaper of the present invention is provided with an outer fastening means and with an inner fastening means. When the elasticized disposable diaper is placed around the waist of the wearer the waist portions of the elasticized disposable diaper are made to overlap. The outer fastening means affixes the overlapping portions of the waist portions to each other and maintains them in contact with each other. The inner fastening means limits and preferably prevents shifting of the overlapping portions thereby maintaining a good fit about the leg and waist of the wearer. The resulting disposable diaper thereby exhibits improved urine and feces containment characteristics when compared to prior art diapers.

The outer fastening means prevents separation of the overlapping waist portions. Thus, the outer fastening means must resist the tensile and peel forces encountered when the diaper is worn. Adhesive tapes as are well known in the disposable diaper art are suitable for use as the outer fastening means.

The inner fastening means may take many forms. Any means whereby shifting of the overlapping portions of the waist is limited and preferably prevented is suitable as an inner fastening means. For example, the inner fastening means may be an area which is covered with an adhesive so that when the waist portions of the diaper are overlapped they adhere to each other. Alternatively, the inner fastening means may comprise an area on one of the waist portions which when brought into contact with the other overlapping waist portion becomes mechanically entangled therewith. further, the inner fastening means may be of a type that is either passive (i.e., requiring no special action by the diaper user) or active (i.e., requiring the diaper user to take action to activate the inside fastening means).

DESCRIPTION OF A PREFERRED EMBODIMENT

Figure 1:
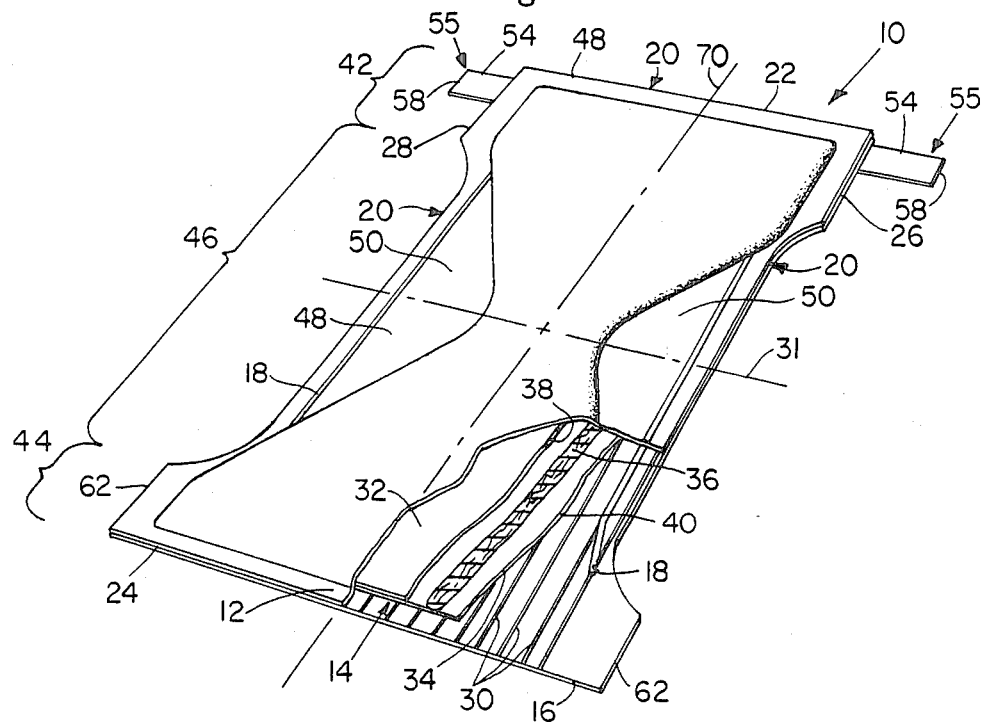
FIG. 1 is a partially cutaway perspective view of an elasticized disposable diaper incorporating the present invention.

Referring now to the drawings, there is shown a preferred embodiment of the present invention as it would be used in a disposable diaper intended to be worn by an infant. As used herein, the term "disposable diaper" refers to a garment generally worn by infants or incontinent persons, which is drawn up between the legs and fastened about the waist of the wearer and further, which is intended to be discarded after a single use (i.e., it is not intended to be laundered or otherwise restored and reused).

FIG. 1 is a partially cut away perspective view of the disposable diaper 10 of the present invention prior to its being folded and placed on the diaper wearer by the diaper user. As can be seen in FIG. 1, a preferred diaper 10 basically comprises a liquid permeable topsheet 12, an absorbent means 14, a liquid impermeable backsheet 16 and elastic member 18. While the topsheet 12, absorbent means 14, liquid impermeable backsheet 16, and elastic member 18 may be assembled in a variety of well known configurations, a preferred disposable diaper configuration is described generally in U.S. Pat. No. 3,860,003 entitled "Contractable Side Portions for Disposable Diaper", which issued to K. B. Buell on Jan. 14, 1975, and which patent is incorporated herein by reference.

Figure 2:
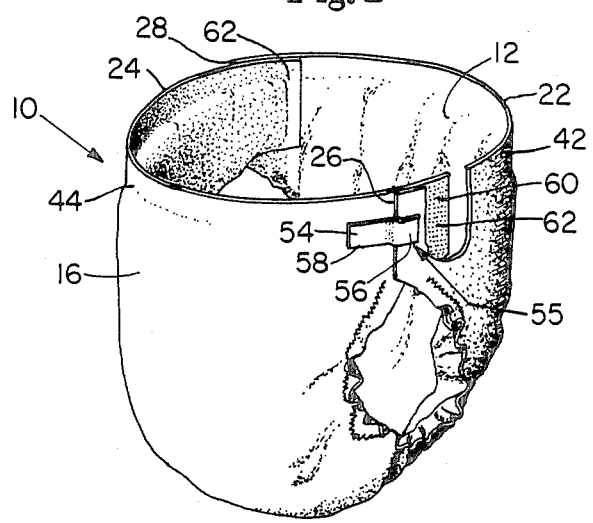
FIG. 2 is a partially cutaway perspective view showing the disposable diaper in FIG. 1 in the configuration it would assume when placed on a wearer.

FIG. 1 and 2 show a preferred embodiment of the diaper 10 in which the topsheet 12 and the backsheet 16 are coextensive and have length and width dimensions generally larger than those of the absorbent means 14. The topsheet 12 is superposed on the backsheet 16 thereby forming a periphery 20 of diaper 10. The periphery 20 defines the outer periphery or, in other words, the outer extent of the diaper 10. The periphery 20 comprises first end 22, second end 24, first longitudinal side 26, and second longitudinal side 28.

The topsheet 12 may be affixed to the backsheet 16 in any suitable manner as is well known in the diaper manufacturing art. In a preferred embodiment a multiplicity of longitudinal adhesive bands 30 of hot-melt adhesive are applied along the full length of the backsheet 16 generally parallel to the longitudinal centerline 70 of the backsheet 16. The longitudinal adhesive bands 30 serve to affix the topsheet 12 to the backsheet 16 at those points where these three components come together. The extent and location of the points where the topsheet 12, backsheet 16, and longitudinal adhesive bands 30 come together will depend on the spacing between the longitudinal adhesive bands 30 and on the distance the topsheet 12 and the backsheet 16 extend beyond the absorbent means 14. The number of longitudinal adhesive bands 30 and the spacing therebetween should be sufficient to securely bond the topsheet 12 to the backsheet 16 in the area between the periphery 20 and the edge of the absorbent means 14.

A hot-melt adhesive suitable for use as longitudinal adhesive bands 30 is manufactured by Eastman Chemical Products Company, of Kingsport, Tenn. and marketed under the tradename Eastobond A-3. It will be noted that the above described manner of affixing the topsheet 12 to the backsheet 16 causes the topsheet 12 to be affixed to the backsheet 16 intermittently along the first and second ends, 22 and 24. The absorbent means 14 is thereby encased between the topsheet 12 and the backsheet 16. Of course, many alternative methods of affixing the topsheet 12 to the backsheet 16 may be used with satisfactory results. For example, the topsheet 12 may be affixed to the backsheet 16 indirectly rather than directly as shown in FIG. 1. Thus, an intermediate member may be used to affix the topsheet 12 to the backsheet 16.

The diaper 10 has first and second waist portions 42 and 44 extending, respectively, from the first end 22 and the second end 24 of the diaper periphery 20 toward the lateral centerline 31 of the diaper 10 a distance from about 1/5 to about ⅓ the length of the diaper. The waist portions 42 and 44 comprise those portions of the diaper 10 which, when worn, encircle the waist of the wearer. The crotch portion 46 is that portion of the diaper 10 between first and second waist portion 42 and 44, and comprises that portion of the diaper 10 which, when worn, is positioned between the legs of the wearer and covers the lower torso of the wearer.

The absorbent means 14 may be any means which is generally compressible, conformable, non-irritating to the wearer's skin, and which is capable of absorbing and retaining liquids. A preferred absorbent means 14 has first and second opposed faces 32 and 34 respectively and comprises an absorbent layer 36 and first and second tissue layers 38 and 40, respectively. The first and second tissue layers 38 and 40 overlay the major surfaces of the absorbent layer 36 to form the first and second opposed faces 32 and 34 of the absorbent means 14.

The absorbent layer 36 is intended to absorb and contain liquid and may be manufactured in a wide variety of sizes and shapes (e.g., rectangular, hourglass, etc.) and from a wide variety of liquid absorbent materials commonly used in disposable diapers, such as comminuted wood pulp which is generally referred to as airfelt. Other liquid absorbing materials may also be used in the manufacture of the absorbent layer 36 such as a multiplicity of plies of creped cellulose wadding, absorbent gelling material, absorbent foams or sponges, or any equivalent material or combination of materials. The total absorbent capacity of the absorbent layer 36 should, however, be compatible with the design liquid loading in the intended use of the disposable diaper 10.

Further, the size and absorbent capacity of the absorbent layer 36 may be varied to accommodate wearers ranging from infants through adults.

The preferred embodiment of diaper 10 illustrated in FIGS. 1 and 2 has an hourglass shaped absorbent layer 36, and is intended to be worn by infants ranging in weight from about 12 to about 26 pounds (about 5 kgs. to about 12 kgs.) The absorbent layer 36 is, therefore, a batt of airfelt approximately 16 inches (41 cm) long when measured along the longitudinal centerline, approximately 12 inches (32 cm) across the first and second ends 22 and 24, and approximately 4 inches (10 cm) across the narrowest part of the crotch portion 46. The absorptive capacity of the airfelt used for the absorbent layer 36 is sufficient to absorb and retain from about 8 to about 16 grams of water per gram of absorbent material. Accordingly, the airfelt used in the preferred embodiment shown in FIGS. 1 and 2 weighs from about 30 to about 56 grams and has a generally uniform caliper. It should be understood, however, that the size, shape, configuration, and total absorbent capacity of the absorbent layer 36 may be varied to accommodate wearers ranging from infants through adults. Therefore, the dimensions, shape, and configuration of the absorbent layer 36 may be varied (e.g. the absorbent layer 36 may have a varying caliper, or a hydrophilic gradient, or may contain absorbent gelling materials).

The first and second tissue layers, 38 and 40, are intended to improve the tensile strength of the absorbent core 14 and to reduce the tendency of the absorbent layer 36 to split, lump or ball when wetted. The first and second tissue layers, 38 and 40, also help to improve lateral wicking of liquids, thereby providing a more even distribution of liquid in the absorbent layer 36. While a number of materials and manufacturing techniques may be used to manufacture the first and second tissue layers, 38 and 40, satisfactory results have been obtained with sheets of tissue paper having a basis weight of approximately 10 pounds per 3000 square feet (16 gms per square meter) and having an air permeability of approximately 100 cubic feet per minute per square foot (30 cubic meters per minute per square meter) over a 0.5 inch (13 mm) water pressure drop. While the first and second tissue layers, 38 and 40, are preferably coterminous with the absorbent layer 36, they may have different dimensions, a different configuration, or they may be omitted entirely.

The absorbent means 14 is superimposed on the backsheet 16 and is preferably affixed thereto by any means as is well known in the diaper art. For example, the absorbent core 14 may be secured to the backsheet 16 by a uniform continuous layer of adhesive, a patterned layer of adhesive, or an array of lines or spots of adhesive. In the preferred embodiment illustrated in FIGS. 1 and 2 the longitudinal adhesive bands 30 are used to affix the absorbent core 14 to the backsheet 16.

The backsheet 16 is impermeable to liquids and prevents liquids absorbed by the absorbent means 14 from wetting the undergarments, clothing, bedding, and other objects which contact the wearer of the disposable diaper 10. Preferably the backsheet 16 is a polyethylene film of from about 0.0005 to about 0.002 inchese (about 0.012 to about 0.051 mm) thick, although other flexible, liquid impermeable materials may also be used. As used herein, the term "flexible" refers to materials which are compliant and which readily conform to the shape and contours of the human body. A suitable polyethylene film is manufactured by Monsanto Chemical Company and marketed in the trade as Film No. 8020. The backsheet 16 is preferably embossed and/or matte finished to provide a more clothlike appearance. Further, the backsheet 16 may have passages which permit vapors to escape from the absorbent means 14 while still preventing liquid from passing through the backsheet 16.

In a preferred embodiment, the backsheet 16 has a modified hourglass shape extending beyond the absorbent layer 36 a minimum distance of at least about 0.5 inches (about 1.3 cm) around the entire diaper periphery 20. The marginal portion 48 is that portion of the diaper 10 between the diaper periphery 20 and the edge of the absorbent layer 36 and comprises longitudinal marginal portions 50 adjacent first and second longitudinal sides 26 and 28, respectively in the crotch portion 46.

The topsheet 12 is compliant, soft feeling, and non-irritating to the wearer's skin and prevents the wearer of the diaper 10 from contacting the absorbent core 14. Further, the topsheet 12 is liquid permeable permitting liquids to readily penetrate through its thickness. A suitable topsheet 12 may be manufactured from a wide range of materials, such as natural fibers (e.g., wood or cotton fibers), synthetic fibers (e.g., polyester, polyethylene, polypropylene), or a combination thereof. Alternatively, the topsheet 12 may be a foam, such as the reticulated foams which are well known in the art or any of the formed films which are also well known in the art.

The topsheet 12 is compliant, soft feeling, and non-irritating to the wearer's skin and prevents the wearer of diaper 10 from contacting the absorbent core 14. Further, the topsheet 12 is liquid permeable permitting liquids to readily penetrate through its thickness. A suitable topsheet 12 may be manufactured from a wide range of materials, such as natural fibers (e.g., wood or cotton fibers), synthetic fibers (e.g., polyester, polypropylene), or a combination thereof. Alternatively, topsheet 12 may be a foam, such as the reticulated foams which are well known in the art or any of the formed films which are also well known in the art.

A number of manufacturing techniques can be used to manufacture the topsheet 12. For example, the topsheet 12 may be woven, nonwoven, spunbonded, carded, or the like. A preferred topsheet 12 is carded, and thermally bonded by means well known to those skilled in the nonwoven fabrics art. Preferably the topsheet 12 has a weight of from about 18 to about 25 grams per square yard, a minimum dry tensile strength of at least about 400 grams per centimeter in the machine direction and a wet tensile strength of at least about 55 grams per centimeter in the cross machine direction.

The elastic members 18 are affixed to the diaper 10 along both longitudinal marginal portions 50 so that they tend to draw and hold the diaper 10 against the legs of the wearer. Thus, when worn the diaper 10 will have elasticized leg openings. While this result may be accomplished by any of several means as are well known in the diaper art a particularly preferred diaper construction incorporating elastic strips is described in detail in the hereinbefore referenced U.S. Pat. No. 3,860,003. In addition, a method and apparatus suitable for manufacturing a disposable diaper having elastic leg bands are described in U.S. Pat. No. 4,081,301 entitled "Method and Apparatus for Continuously Attaching Discrete, Stretched Elastic Strands to Predetermined Isolated Portions of Disposable Absorbent Products"

which issued to K. B. Buell on Mar. 28, 1978 and which patent is incorporated herein by reference.

Relating the teachings of U.S. Pat. No. 3,860,003 to the preferred embodiment shown in FIGS. 1 and 2 it can be seen that elastic members 18 are operatively associated with both longitudinal marginal portions 50 in the crotch portion 46 in an elastically contractible condition so that in a normally unrestrained configuration the elastic members 18 effectively contract or gather the longitudinal marginal portions 50.

As used herein the term "operatively associated with" refers to two or more components which act together. In the preferred embodiment shown in FIGS. 1 and 2 the elastic members 18 are operatively associated with both longitudinal marginal portions 50 in the crotch portion 46. Thus, the elastic members 18 are affixed to the longitudinal marginal portions 50 so as to cause the longitudinal marginal portions 50 in the crotch portion 46 to be contracted or gathered. A suitable method for incorporating elastic members 18 into a disposable diaper is described in the aforesaid U.S. Pat. No. 4,081,301.

In the preferred embodiment illustrated the elastic members 18 are affixed to a portion of the backsheet 16 in the longitudinal marginal portions 50. A suitable adhesive will be flexible and of sufficient adhesiveness to hold the elastic member 18 to the backsheet 16 while the elastic member 18 is stretched. An adhesive which has been used with satisfactory results is manufactured by Findley Adhesives Corporation of Elm Grove, Wis. and is marketed under the tradename Findley 581-334-01.

The elastic members 18 can be operatively associated with the longitudinal marginal portions 50 in an elastically contractible condition in at least two ways. For example, the elastic member 18 may be stretched and while in the stretched condition affixed to the uncontracted and unstretched longitudinal marginal portions 50. Alternatively, the longitudinal marginal portions 50 may be contracted (e.g., by pleating) and then affixing the unstretched elastic member 18 to the contracted longitudinal marginal portions 50.

Suitable elastic members 18 may be manufactured from a wide variety of elastic materials such as natural rubber, or elastomeric films such as Kraton, ethylene propylene-dimonomer, and polyurethane.

In addition, the elastic member 18 may take a multitude of configurations. For example, the width of the elastic members 18 may be varied from about 0.015 inches to 1.0 inches (0.38 mm–25 mm) or more; the elastic members 18 may comprise a single strip of elastic material or may comprise several parallel or non parallel strips of elastic material; or the elastic members 18 may be rectilinear or curvilinear. Still further, the elastic member 18 may be affixed to the diaper 10 in any of several ways which are well known in the art. For example, the elastic members 18 may be ultrasonically bonded or heat sealed into the diaper using a variety of bonding patterns or the elastic members 18 may simply be glued to the diaper 10. The outer fastening means with inner fastening means are particularly useful for preventing gapping at the elasticized leg openings caused by curvilinear elastic members.

One material which has been found to work well as an elastic member 18 is an elastic tape having a cross section of 0.007 inches by 0.25 inches (about 0.18 mm by about 6.4 mm) and which is manufactured from natural rubber. Such a product is marketed by Easthampton Rubber Thread Company under the tradename L-1900 rubber compound. The preferred elastic member 18 produces a tensile force of about 100 grams when stretched 100 percent from its relaxed condition.

The diaper 10 is provided with an outer fastening means 54 for maintaining the first and second waist portions 42 and 44 in an overlapping configuration when the diaper 10 is worn. Thus, the diaper 10 is fitted to the wearer and a side closure formed.

More specifically, the outer fastening means 54 affixes the first waist portion 42 to the second waist portion 44 thereby maintaining the first and second waist portions 42 and 44 in an overlapping configuration. Thus, the outer fastening means 54 must be affixed to both the first waist portion 42 and to the second waist portion 44 in a manner and with a strength that is sufficient to resist the forces acting to cause the first and second waist portions 42 and 44 to separate during wearing.

The outer fastening means 54 may comprise any of the well known means for achieving a side closure such as Velcro strips or patches, buttons, or snaps. A preferred outer fastening means 54 is an adhesive tape 55 as is well known in the diaper art.

Any of the well known configurations and constructions may be used as the adhesive tape 55. For example, the adhesive tape 55 may be a single use tape or a multiple use tape (i.e., refastenable). A preferred adhesive tape 55 is a Y-shaped tape as described in detail in U.S. Pat. No. 3,848,594 entitled Tape Fastening System for Disposable Diaper which issued to K. B. Buell on Nov. 19, 1974, which patent is incorporated herein by reference. The outer fastening means 54 are provided at both the first and second longitudinal sides, 26 and 28 respectively.

The preferred adhesive tape 55 illustrated in FIG. 2 has a manufacturers end 56 and a users end 58. The manufacturers end 56 is that end of the adhesive tape 55 which the manufacturer of the diaper 10 affixes to the diaper 10 while the users end 58 is that end of the adhesive tape 55 which the user affixes to the diaper 10 when fitting the diaper 10 to the wearer. The manufacturers end 56 is affixed to the first waist portion 42 and after fitting the diaper 10 about the waist of the wearer the users end 58 is affixed to the second waist portion 44 thereby causing the diaper 10 to encircle the waist of the wearer and effecting a side closure.

The second waist portion 44 has panels 62. The panels 62 are those portions of the second waist portion 44 which are overlain by the first waist portion 42 when the diaper 10 is fastened about the waist of the wearer. The extent to which the second waist portion 44 is overlain and thus the extent to which panels 62 are formed will depend on the overall dimensions and shape of the diaper 10 and the size of the wearer.

The diaper 10 is provided with an inner fastening means 60 (FIG. 2) for reducing and preferably preventing shifting of the panels 62 and the first waist portion 42 relative to each other. The inner fastening means 60, therefore, resists the shear forces which act to cause the panels 62 to shift their position relative to the first waist portion 42 as the diaper 10 is worn.

As described hereinabove, the diaper 10 is generally fitted to the wearer so that the diaper 10 conforms to the wearers waist and legs thereby providing protection against leakage. It is desirable to maintain the diaper 10 in the configuration in which it is applied so that the conformity about the wearers waist and legs is also maintained. Thus, it is important that the panels 62 be retarded and preferably prevented from shifting their position relative to the first waist portion 42 while the diaper 10 is worn. The purpose of the inner fastening means 60, therefore is to maintain the panels 62 and the first waist portion 42 in the position relative to each other that they assume when the diaper 10 is initially fitted to the wearer.

After the initial placement of the panels 62 against the first waist portion 42 during fitting of the diaper 10 to the wearer the panels 62—first waist portion 42 interface is subjected to shear forces which act in such a manner as to cause the panels 62 and first waist portion 42 to shift position relative to each other. If such a shift in position of the panels 62 and first waist portion 42 occurs the conformity of the diaper 10 about the waist and legs of the wearer will be degraded. Thus, the inner fastening means 60 must have a shear resistance sufficient to resist the shear forces acting on the panels 62—first waist portion 42 interface. These shear forces are induced by the elastic members 18 and by the movements of the diaper wearer.

As used herein the term "shear forces" refers to the forces encountered during the wearing of the diaper 10 and which forces tend to cause the panels 62 to shift position with respect to the first waist portion 42. Shear forces are to be distinguished from peel forces which cause the panels 62 to separate or move away from the first waist portion 42. Peel forces are resisted by the outer fastening means 54 while the shear forces are resisted by the inner fastening means 60.

While the inner fastening means 60 may take many alternative configurations it has been found that an inner fastening means 60 capable of resisting shear forces of at least about 500 grams and preferably at least about 750 grams and most preferably at least about 1000 grams works well. The shear resistance of the inner fastening means 60 may readily be determined in accordance with the procedure described hereinafter.

The inner fastening means 60 may either be integral (i.e., a discrete separate element affixed to diaper 10) or unitary (i.e., a single piece of material that is neither divided nor discontinuous) with the panels 62, or with the first waist portion 42, or with both the panels 62 and the first waist portion 42. For example, the surface of the panels 62 which contacts the first waist portion 42 may be manufactured so as to mechanically engage that portion of the first waist portion 42 which overlays the panels 62. Alternatively the inner fastening means 60 may comprise a layer of adhesive applied to the panels 62 which adhesive has a high enough shear resistance to prevent the panels 62 from shifting with respect to the overlapping portions of the first waist portions 42. Alternatively, the adhesive may be applied to the first waist portion 42. It is not necessary for the inner fastening means 60 to have a high resistance to peel since the overlapping portions of the first and second waist portion 42 and 44, are maintained against each other by the outer fastening means 54.

In the preferred embodiment illustrated the inner fastening means 60 is integral with the panels 62 comprising a layer of material affixed to the panels 62 and capable of mechanically engaging the topsheet 12 (i.e., the layer of material becomes entangled in the fibers of the topsheet 12). A suitable material is marketed by 3M Corporation, St. Paul, Minn., under the tradename SJ 3492. An alternatively preferred inner fastening means 60 comprises a layer of adhesive such as that marketed by 3M of St. Paul, Minn. under the tradename OEM 1524 which is applied to the panels 62.

The inner fastening means 60 is preferably affixed to both panels 62 and covers an area 1 inch wide (i.e., generally perpendicular to longitudinal centerline 20) by 2.5 inches long (i.e., generally parallel to longitudinal centerline 70) at the corners of the diaper 10.

The shear resistance of the inner fastening means 60 is a measure of the ability of the inner fastening means 60 to resist shear forces and thus prevent the panels 62 from shifting position with respect to the first waist portion 42. The shear resistance of the inner fastening means 60 may be determined using any method which measures the force required to first initiate movement between the panels 62 and the first waist portion 42 at a contact pressure of about 17 grams/square centimeter. The following procedure for determining the shear resistance of the inner fastening means 60 was used with good results. Two samples are cut from the diaper 10. The first sample is cut from one of the panels 62 and comprises that portion of the panel 62 which is overlapped by the first waist portion 42 when the diaper 10 is worn and the second sample is cut from the first waist portion 42 and comprises that portion of the first waist portion 42 which overlaps the panel 62 when the diaper is worn. The first sample should have dimensions sufficient to permit it to cover the face of a 63.5 millimeters square sled and the second sample should be at least 63.5 millimeters square. If the inside fastening means 60 has dimensions less than 63.5 millimeters by 63.5 millimeters the samples should be selected so as to encompass as much of the inside fastening means 60 as possible.

Both samples are stripped of any loose or extraneous material such as the absorbent means 14. The first sample is affixed to a friction sled which is about 63.5 millimeters square by about 6.0 millimeters thick and which is covered on at least one surface with a 3.2 millimeters thick, medium-density foam rubber which is wrapped snugly around the sled and fastened in position. The wrapped sled and additional weights weigh 710±5 grams. In affixing the first sample to the friction sled the inner surface of the backsheet 16 of the first sample is placed against the friction sled. The second sample is affixed to a friction platform with the inner surface of the topsheet 12 of the second sample against the friction platform.

The covered friction sled is then set on the second sample thus simulating the conditions when the diaper 10 is worn. A shear force is applied to the friction sled, along a line parallel to the friction platform and the force required to first initiate a sliding of the friction sled relative to the friction platform is the shear resistance of the inner fastening means 60. The shear force may be applied and measured using any technique or apparatus that will be known to those skilled in the testing art. It has been found, however, that the shear resistance of the inside fastening means may easily be determined using a tensile tester of the types manufactured by Instron Corporation of Canton, Mass. and marketed under the tradename Instron 1101-TM, 1102-TMS, 1122 and 1130.

What is claimed is:
1. A disposable diaper comprising:
    a liquid permeable topsheet;
    a liquid impermeable backsheet, said backsheet being affixed to said topsheet;

an absorbent means for absorbing liquids, said absorbent means being encased between said topsheet and said backsheet;

longitudinal marginal portions adjacent both longitudinal sides of the disposable diaper;

elastic members operatively associated with both of said longitudinal marginal portions;

a first waist portion at one end of the disposable diaper and a second waist portion at the opposite ends of the disposable diaper, said second waist portion having a first panel and a second panel;

an outer fastening means for maintaining said first waist portion and said second waist portion in an overlapping configuration, at least a portion of said outer fastening means being adjacent to a longitudinal side of the disposable diaper; and, an inner fastening means for resisting shear forces, said inner fastening means being positioned adjacent to said panels.

2. The disposable diaper of claim 1 wherein said inner fastening means has a shear resistance of at least about 500 grams.

3. The disposable diaper of claim 1 wherein the shear resistance of said inner means is at least about 750 grams.

4. The disposable diaper of claim 1 wherein the shear resistance of said inner means is about 1000 grams.

5. The disposable diaper of claim 1 wherein said inner fastening means comprises a layer of adhesive applied to said first panel and to said second panel.

6. The disposable diaper of claim 1 wherein said inner fastening means comprises a layer of adhesive applied to said first waist portion.

7. The disposable diaper of claim 1 wherein said inner fastening means comprises segments of said first panel and said second panel having a surface texture which engages said first waist portion.

8. The disposable diaper of claim 1 wherein said elastic members are curvilinear.

9. The disposable diaper of claim 1 wherein said elastic members are rectilinear.

* * * * *